United States Patent [19]

Kitamura et al.

[11] Patent Number: 6,147,079
[45] Date of Patent: Nov. 14, 2000

[54] N-(4-ACETYL-1-PIPERAZINYL)-4-FLUOROBENZAMIDE HYDRATE

[75] Inventors: Satoshi Kitamura, Suita; Hisashi Mimura; Hiroshi Yamasaki, both of Kobe; Yukihisa Baba, Nishinomiya, all of Japan

[73] Assignee: Fujisawa Pharmaceutical Co., Ltd., Osaka, Japan

[21] Appl. No.: 09/319,271

[22] PCT Filed: Dec. 5, 1997

[86] PCT No.: PCT/JP97/04451

§ 371 Date: Jun. 14, 1999

§ 102(e) Date: Jun. 14, 1999

[87] PCT Pub. No.: WO98/25914

PCT Pub. Date: Jun. 18, 1998

[30] Foreign Application Priority Data

Dec. 12, 1996 [JP] Japan .................................. 8-331784

[51] Int. Cl.[7] ...................... A61K 31/495; C07D 241/04; A61P 25/28
[52] U.S. Cl. ........................ 514/255.01; 544/382
[58] Field of Search .............. 514/255; 544/382, 544/255.01

[56] References Cited

U.S. PATENT DOCUMENTS 5,250,528  10/1993  Oku, et al. .

FOREIGN PATENT DOCUMENTS 0 436 734 A1  7/1991  European Pat. Off. .

OTHER PUBLICATIONS

Yamazaki, M. et al. The Journal of Pharmacology and Experimental Therapeutics. vol. 279, No. 3, Dec. 1996, pp. 1157–1173.

*Primary Examiner*—Michael G. Ambrose
*Attorney, Agent, or Firm*—Oblon, Spivak, McClelland, Maier & Neustadt, P.C.

[57] ABSTRACT

Hydrates of N-(4-acetyl-1-piperazinyl)-4-fluorobenzamide, which are stable against heat, light, and humidity, are described. The material is easy to handle under ordinary interior humidity conditions. N-(4-acetyl-1-piperazinyl)-4-fluorobenzamide hydrate is useful as a medicament in the treatment of amnesia and senile dementia.

16 Claims, 5 Drawing Sheets

N-(4-ACETYL-1-PIPERAZINYL)-4-FLUOROBENZAMIDE HYDRATE

This application is a 371 of PCT/JP97/0445/ filed Dec. 5, 1997.

TECHNICAL FIELD

This invention relates to N-(4-acetyl-1-piperazinyl)-4-fluorobenzamide hydrate which is useful as a medicament.

BACKGROUND ART

N-(4-Acetyl-1-piperazinyl)-4-fluorobenzamide having The following chemical formula:

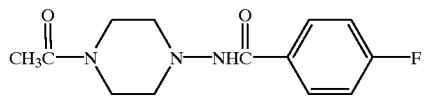

was first described by the applicant of the instant application in WO 91/01979 and is a per se known compound. This compound has the potentiation of the cholinergic activity and is known to have excellent antidementia and antiamnesic actions.

DISCLOSURE OF INVENTION

This invention relates to N-(4-acetyl-1-piperazinyl)-4-fluorobenzamide hydrate.

One object of this invention is to provide N-(4-acetyl-1-piperazinyl)-4-fluorobenzamide in a form easy to handle under ordinary interior humidity conditions and resistant to stress testings, i.e. N-(4-acetyl-1-piperazinyl)-4-fluorobenzamide hydrate.

Another object of this invention is to provide an agent and a pharmaceutical composition comprising, as an active ingredient, said hydrate.

A further object of this invention is to provide a therapeutical method for the treatment and/or prevention of disorders in the central nervous system For human beings, and more particularly in the treatment and/or prevention of amnesia, dementia, senile dementia and the like.

More particularly, the inventors of this invention endeavored in earnest to accomplish the above object and discovered the hydrate form of N-(4-acetyl-1-piperazinyl)-4-fluorobenzamide which can be handled with ease under ordinary interior humidity conditions and stable even under accelerated heat, humidity, and light exposure test conditions. This invention has been accomplished on the basis of the above finding.

Thus, N-(4-acetyl-1-piperazinyl)-4-fluorobenzamide free of water of crystallization undergoes change in water content by absorbing moisture under ordinary interior humidity conditions and the rate of its moisture absorption also varies with the ambient relative humidity, thus offering the disadvantage that it cannot be easily handled in the laboratory room and the pharmaceutical manufacturing room. Therefore, the inventors explored for a stable form of N-(4-acetyl-1-piperazinyl)-4-fluorobenzamide which would show little change in water content under ordinary interior humidity conditions and could, therefore, be easily handled in both the laboratory room and the pharmaceutical manufacturing room and discovered that the hydrate, preferably the monohydrate (theoretical water content 6.36%), of the above compound shows substantially no change in water content in addition to the advantage that it can be easily handled. Furthermore, this N-(4-acetyl-1-piperazinyl)-4-fluorobenzamide hydrate, preferably monohydrate thereof, is chemically stable even under accelerated heat, humidity, and light exposure test conditions. It was also confirmed that N-(4-acetyl-1-piperazinyl)-4-fluorobenzamide hydrate, preferably monohydrate thereof, remains chemically stable without undergoing crystallographic change in the accelerated heat, humidity, and light exposure tests. The following are experimental findings substantiating the above description.

In this invention, it is to be noted that N-(4-acetyl-1-piperazinyl)-4-fluorobenzamide hydrate may include all hydrate containing one or more water molecule(s) such as monohydrate, dihydrate, trihydrate, etc., in which preferable one is monohydrate.

Experiment 1: Moisture Absorption Test

1) Method

About 0.2 g of N-(4-acetyl-1-piperazinyl)-4-fluorobenzamide monohydrate was accurately weighed into a weighing bottle about 3 cm in diameter and placed in a desiccator controlled at a relative humidity (R.H.) value of 43% with a saturated potassium carbonate solution. This test sample was stored in a constant-temperature room at 25° C. for 24 hours and the change in water content was sequentially monitored.

2) Results

TABLE 1

| Time (Hr) | 0 | 1 | 2 | 3 | 4 | 5 | 6 | 24 |
|---|---|---|---|---|---|---|---|---|
| Water content (%) | 6.23 | 6.23 | 6.23 | 6.27 | 6.23 | 6.27 | 6.23 | 6.18 |

The above results indicate that N-4(-acetyl-1-piperazinyl)-4-fluorobenzamide monohydrate undergoes little change in water content in an environment of 43% R.H. even for as many as 24 hours.

Experiment 2: Stability in Solid State

1) Method

N-(4-Acetyl-1-piperazinyl)-4-fluorobenzamide monohydrate, 0.2 g, was weighed into an amber-colored No. 1 bottle which was then placed in a desiccator controlled at 75% R.H. with a saturated aqueous solution of sodium chloride and stirred in a minijet oven at 70° C. for 9 days. Separately, 0.2 g of N-(4-acetyl-1-piperazinyl)-4-fluorobenzamide monohydrate was accurately weighed, spread thinly in a dish about 4 cm in diameter, covered with polyvinylidene chloride film, and exposed to a chemical lamp for 24 hours. Using the above 2 samples, the quality parameters of description, water content (K.F. method), infrared spectrum, and liquid chromatographic assay [detector: ultraviolet spectrophotometer (exciting wavelength 254 nm), column: TSK gel ODS-80TM (5 μm) (4.6 mm in. dia.×15 cm long), column temperature: room temperature; mobile phase: water-acetonitrile (4:1), sample concentration: 0.5 mg/ml (solvent: acetonitrile), flow rate: the retention time of N-(4-acetyl-1-piperazinyl)-4-fluorobenzamide adjusted to ca 7 min.) (ca 1.0 ml/min.), infection size: 5 μl] were determined.

2) Results

TABLE 1

| Storage conditions<br>Test parameters | Initial | 70° C.<br>75% R.H.,<br>9 days | Chemical lamp exposure test,<br>24 hrs |
|---|---|---|---|
| Description | White powders | White powders | White powders |
| Water content (%) | 6.23 | 6.40 | 6.10 |
| IR spectrum | — | No change | No change |
| Residue (%) | 100.0 | 100.5 | 99.9 |

Those results indicate that N-(4-acetyl-1-piperazinyl)-4-fluorobenzamide monohydrate is chemically stable against accelerated 70° C., 75% R.H. heat and humidity test and accelerated chemical lamp exposure rest conditions, undergoing no change in crystal morphology.

EXAMPLE 1

N-(4-acetyl-1-piperazinyl)-4-fluorobenzamide (192.0 g) is added to 50% aqueous ethanol (960 ml) and dissolved therein by heating. The solution is filtered when hot and washed with prewarmed 25% aqueous ethanol (384 ml). Then, water (1540 ml) is added under warming and the mixture is cooled gradually under constant stirring. The resulting crystals are collected by filtration and dried in vacuo. The anhydrous N-(4-acetyl-1-piperazinyl)-4-fluorobenzamide thus obtained is allowed to stand for equilibration under a water-filled tray disposed in the bottom stage of a driver at a shelf temperature of 25° C. and a vacuum of 25–30 mmHg to provide N-(4-acetyl-1-piperazinyl)-4-fluorobenzamide monohydrate (183.5 g).

Water Content (K.F. Method):
  6.23% (theoretical value for the monohydrate: 6.36%)
Infrared (IR) Spectrum (Nujol)
  As shown in FIG. 1.
Powder X-ray Diffraction Pattern
  As shown in FIG. 2.
Thermal Analysis (TG/DTA Data)
  As shown in FIG. 3

By subjecting the compound obtained by the above procedure to recrystallization from a saturated chloroform solution, colorless clear platelets can be obtained. X-ray crystallographic analysis of the above crystal crop yielded the crystal structure containing one molecule of water as shown in FIG. 4 and the X-ray diffraction pattern (FIG. 5) calculated from this crystal structure was found to agree well with the powder X-ray diffraction pattern shown in FIG. 2.

Effects of the Invention

N-(4-Acetyl-1-piperazinyl)-4-fluorobenzamide hydrate as provided by this invention undergoes little change in water content under ordinary interior humidity conditions and can, therefore, be easily handled. It has also been established that the hydrate is chemically stable against accelerated heat, humidity and light exposure test conditions, showing no alteration in crystal morphology, either.

For therapeutic purpose, N-(4-acetyl-1-piperazinyl)-4-fluorobenzamide hydrate of the present invention can be used in a form of pharmaceutical preparation containing said compound, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension of emulsion. If desired, there may be included in these preparations, auxiliary substances, stabilizing agents, wetting or emulsifying agents, buffers and other commonly used additives.

While the dosage of N-(4-acetyl-1-piperazinyl)-4-fluorobenzamide hydrate will vary depending upon the age and condition of the patient, an average single dose of about 0.1 mg, 1 mg, 10 mg, 50 mg, 100 mg, 250 mg, 500 mg and 1000 mg of N-(4-acetyl-1-piperazinyl)-4-fluorobenzamide hydrate may be effective for treating the above-mentioned diseases. In general, amounts between 0.1 mg/body and about 1,000 mg/body may be administered per day.

Figure 1:
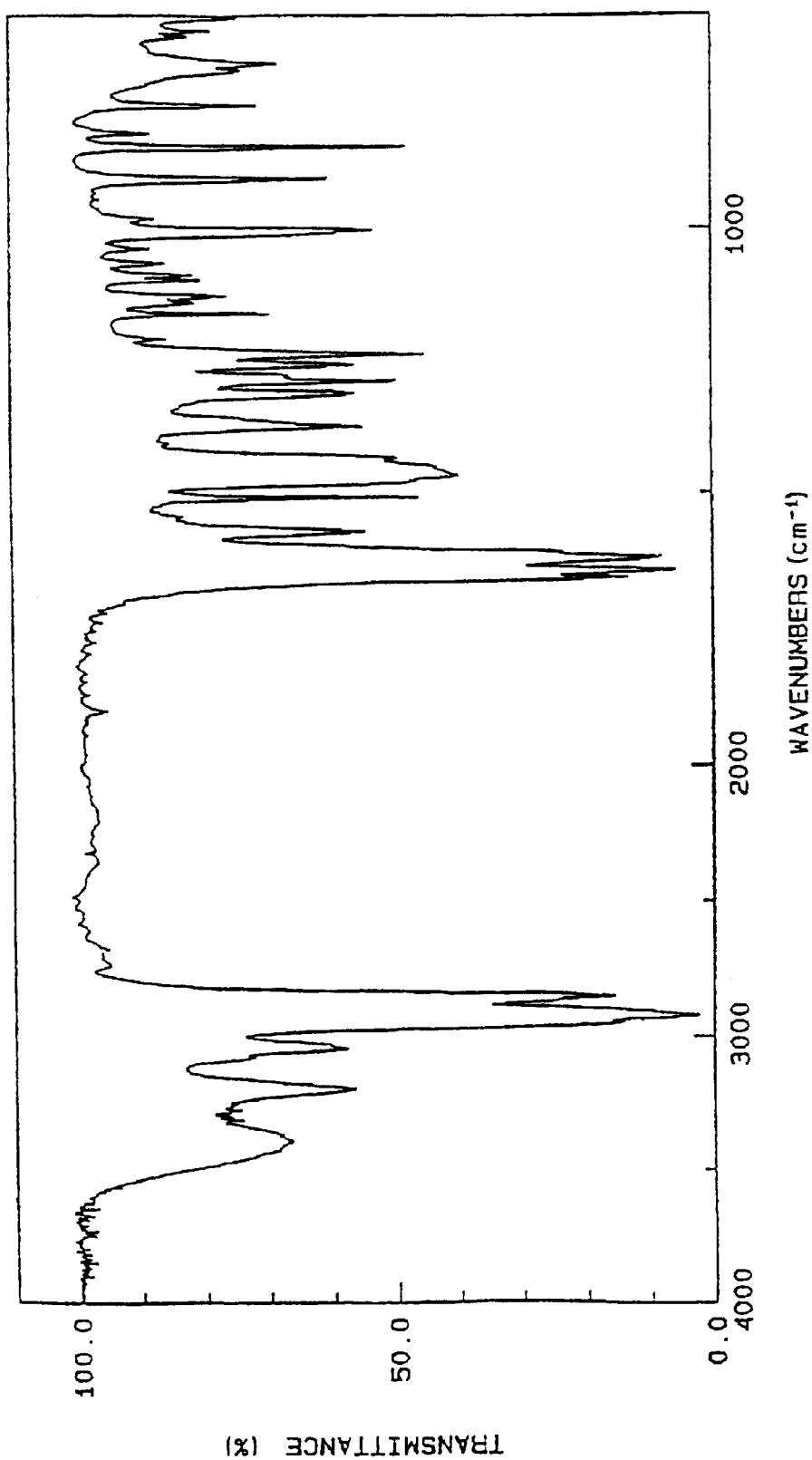
FIG. 1: An infrared absorption spectrum of N-(4-acetyl-1-piperazinyl)-4-fluorobenzamide monohydrate.
Figure 2:
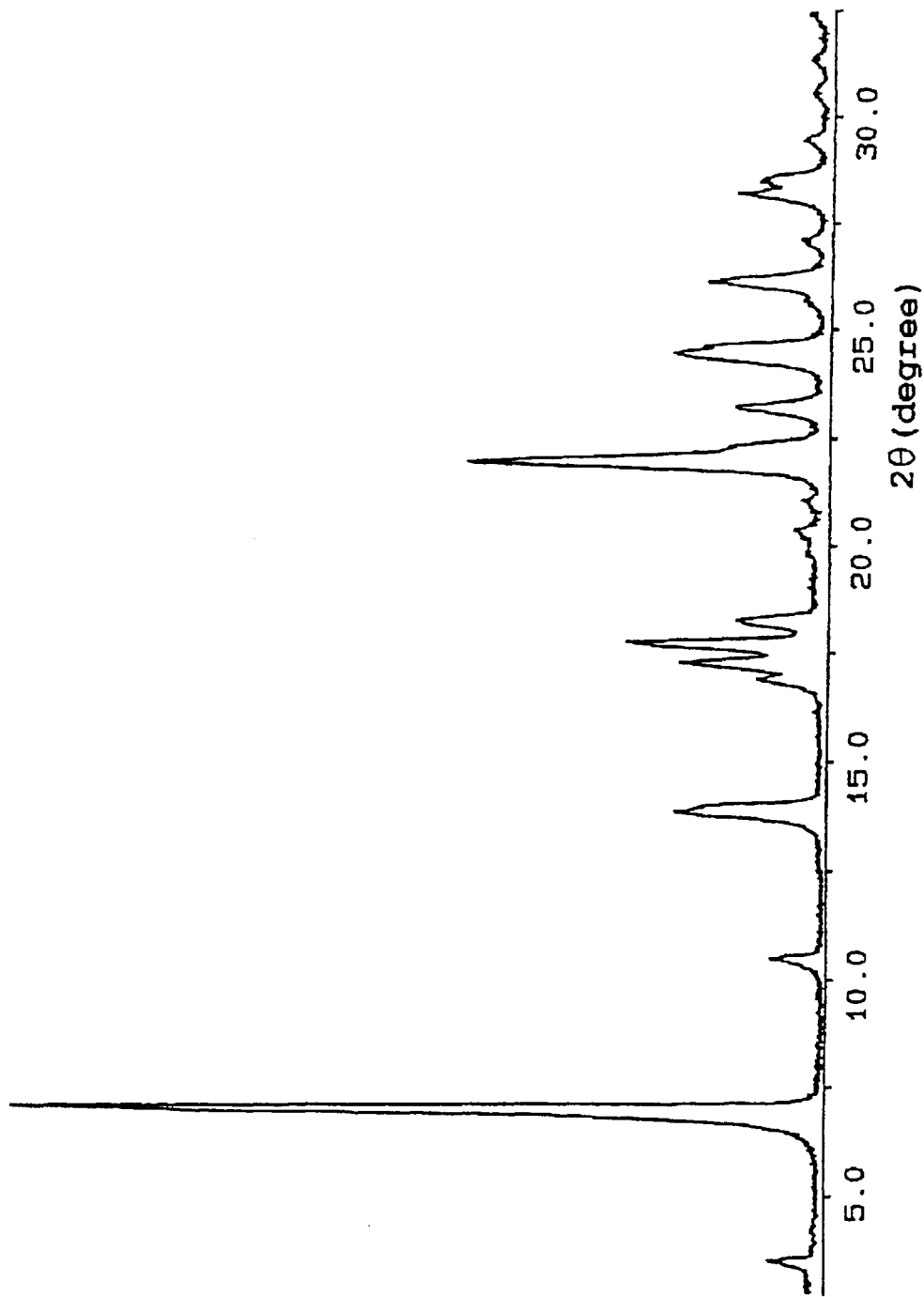
FIG. 2: A powder X-ray diffraction pattern of N-(4-acetyl-1-piperazinyl)-4-fluorobenzamide monohydrate.
Figure 3:
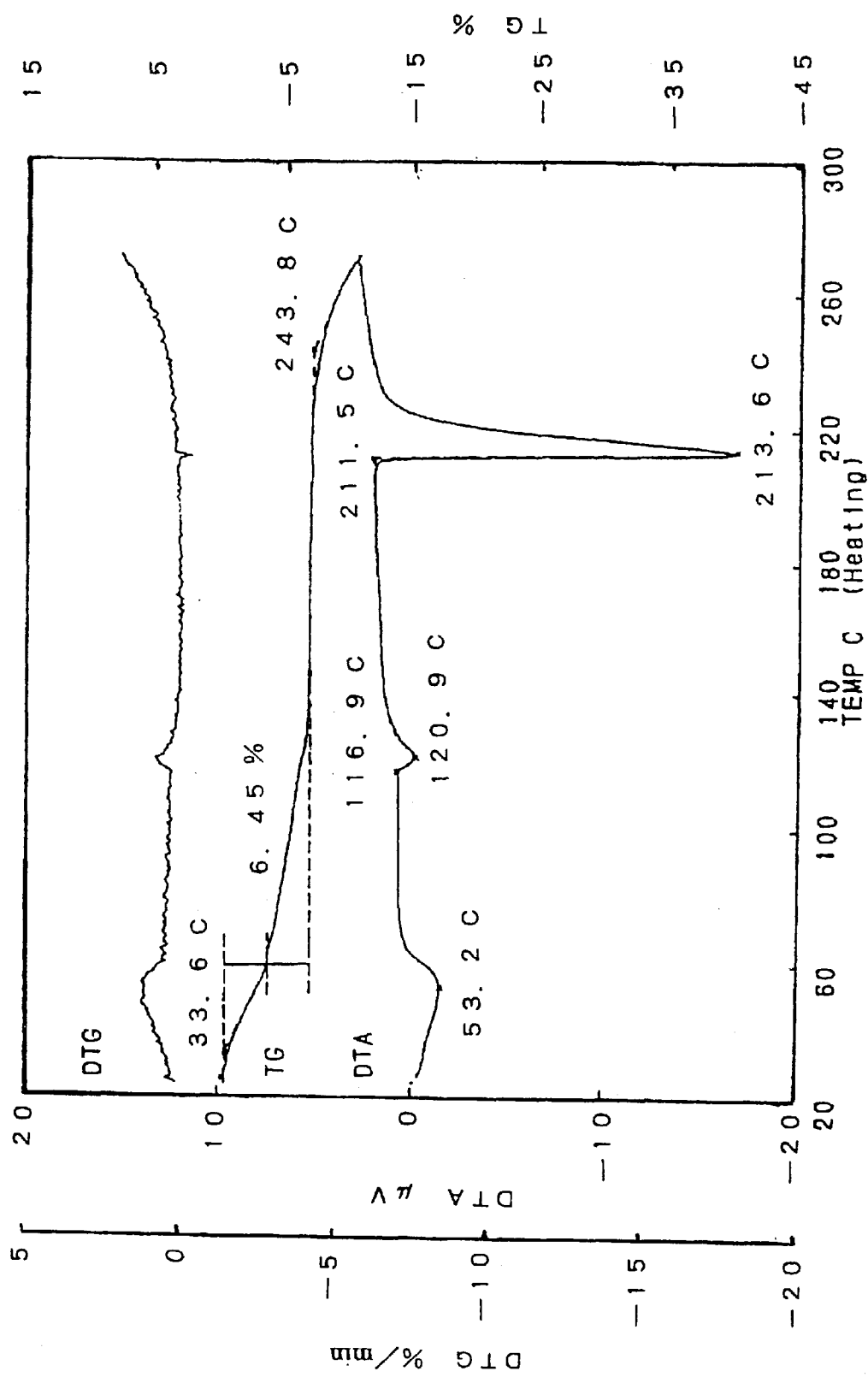
FIG. 3: A thermal analysis (TG/DTA) diagram of N-(4-acetyl-1-piperazinyl)-4-fluorobenzamide monohydrate.
Figure 4:
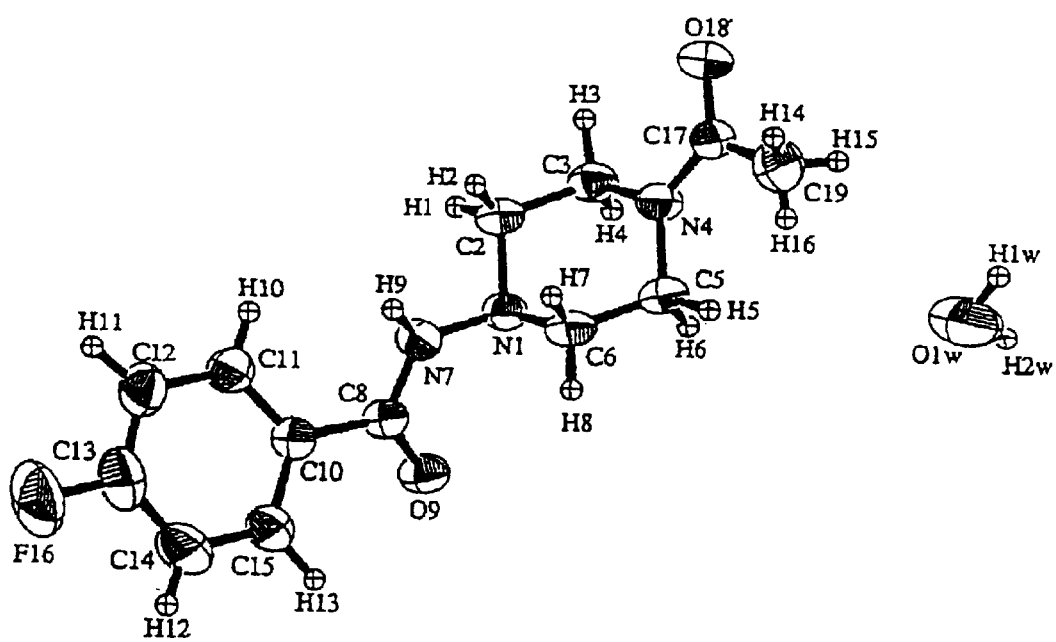
FIG. 4: The three-dimensional structure of N-(4-acetyl-1-piperazinyl)-4-fluorobenzamide monohydrate.
Figure 5:
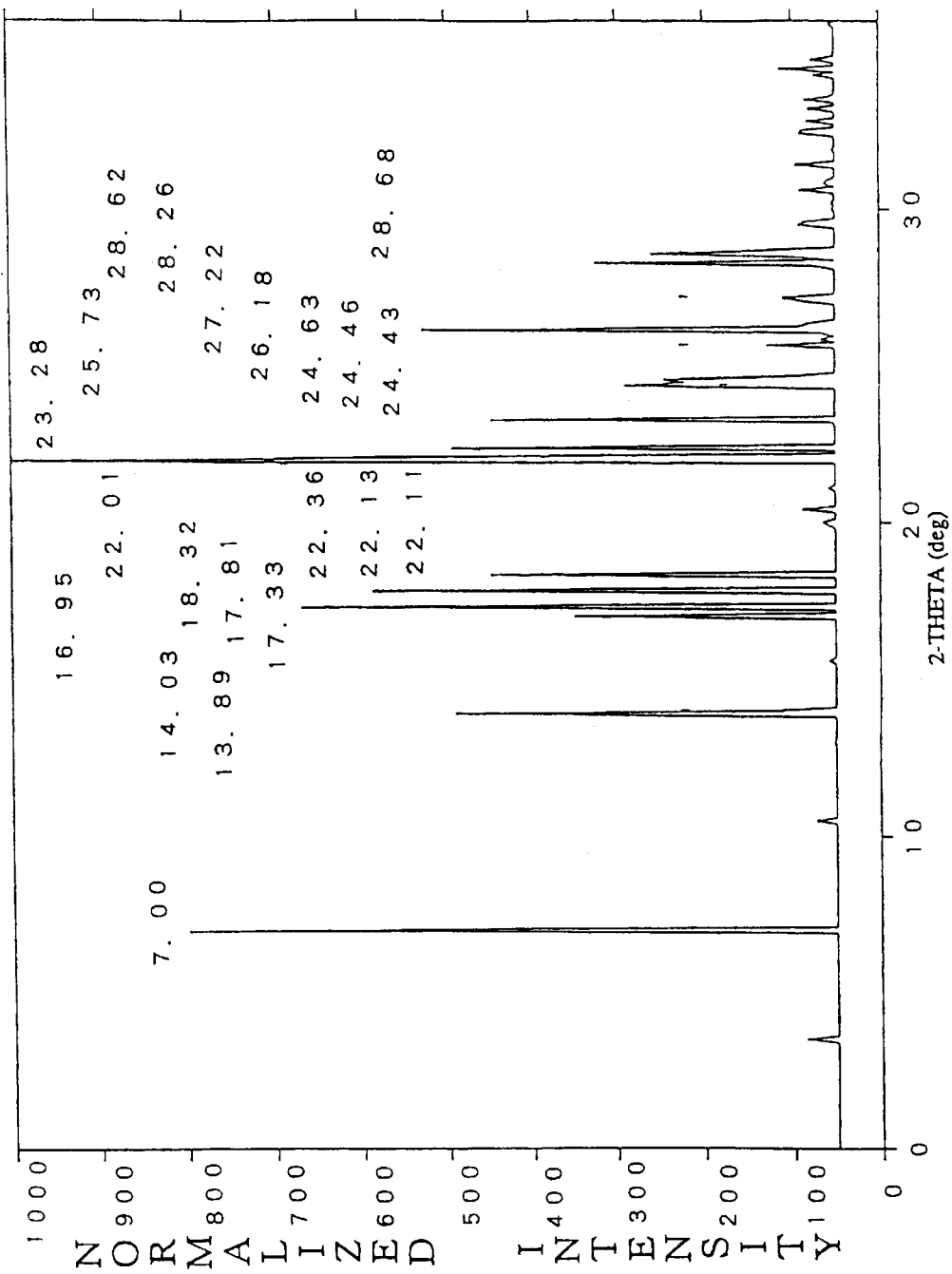
FIG. 5: The X-ray diffraction pattern calculated from the 3-dimensional structure of N-(4-acetyl-1-piperazinyl)-4-fluorobenzamide monohydrate.

What is claimed is:

1. N-(4-Acetyl-1-piperazinyl-4-fluorobenzamide hydrate in the form of a solid.

2. The hydrate of claim 1, which is in the form of a monohydrate.

3. The monohydrate of claim 2, which has the following physical properties:

(i) a powder X-ray diffraction pattern with characteristic peaks around 7.0°, 13.8°, 17.7°, 22.0°, 24.4° and 26.1°, and (ii) an infrared spectrum (Nujol) with absorption bands near 3196, 1641, 1618, 1240 and 849 (cm$^{-1}$).

4. The hydrate of claim 1, which is in the form of a dihydrate.

5. A solid pharmaceutical composition, comprising the hydrate of claim 1 in association with a pharmaceutically acceptable, substantially nontoxic solid carrier or excipient.

6. The composition of claim 5, which is in the form of a capsule, tablet, dragees or granule.

7. A method of preparing a pharmaceutical composition, comprising combining the hydrate of claim 1 with a pharmaceutically acceptable, substantially nontoxic carrier or excipient.

8. The method of claim 7, wherein the carrier or excipient is a solid.

9. The method of claim 7, wherein the carrier or excipient is a liquid.

10. The method of claims 7, wherein the composition is in the form of a solution, suspension or emulsion.

11. The method of claim 7, wherein the composition is in the form of a solid.

12. The method of claim 7, wherein the composition is in the form of a capsule, tablet, dragees or granule.

13. A method of treating amnesia, dementia or senile dementia, comprising administering an effective amount of the composition of claim 5 to a patient in need thereof.

14. The method of claim 13, wherein the patient is a human being.

15. A method of treating amnesia, dementia or senile dementia, comprising:

preparing a pharmaceutical composition according to claim 7, and administering an effective amount of the composition to a patient in need thereof.

16. The method of claim 15, wherein the patient is a human being.

* * * * *